(12) United States Patent
Daynes et al.

(10) Patent No.: US 8,744,574 B2
(45) Date of Patent: Jun. 3, 2014

(54) DEFIBRILLATOR WITH MUTABLE SOUND PROMPTS

(75) Inventors: John Daynes, Redmond, WA (US); Glen Caby, Kirkland, WA (US); Richard C. Nova, Kirkland, WA (US)

(73) Assignee: Physio-Control, Inc., Redmond, WA (US)

( * ) Notice: Subject to any disclaimer, the term of this patent is extended or adjusted under 35 U.S.C. 154(b) by 406 days.

(21) Appl. No.: 13/016,882

(22) Filed: Jan. 28, 2011

(65) Prior Publication Data

US 2012/0109239 A1 May 3, 2012

Related U.S. Application Data

(60) Provisional application No. 61/409,053, filed on Nov. 1, 2010.

(51) Int. Cl.
*A61N 1/39* (2006.01)

(52) U.S. Cl.
CPC ............. *A61N 1/3993* (2013.01); *A61N 1/3925* (2013.01)
USPC .......................................................... 607/5

(58) Field of Classification Search
None
See application file for complete search history.

(56) References Cited

U.S. PATENT DOCUMENTS

| | | | |
|---|---|---|---|
| 6,059,576 A * | 5/2000 | Brann ............................ | 434/247 |
| 6,398,727 B1 * | 6/2002 | Bui et al. ...................... | 600/300 |
| 7,670,263 B2 * | 3/2010 | Ellis et al. ..................... | 482/8 |
| 8,086,320 B2 * | 12/2011 | Saketkhou ...................... | 607/60 |
| 2003/0036044 A1 * | 2/2003 | Pastrick et al. ............... | 434/265 |
| 2003/0233129 A1 * | 12/2003 | Matos ............................. | 607/5 |
| 2004/0027245 A1 | 2/2004 | Schlager | |
| 2004/0102931 A1 * | 5/2004 | Ellis et al. .................... | 702/188 |
| 2007/0162075 A1 * | 7/2007 | O'Hara ........................... | 607/5 |
| 2009/0092260 A1 * | 4/2009 | Powers ........................... | 381/57 |
| 2010/0114218 A1 | 5/2010 | Heath | |
| 2011/0158430 A1 * | 6/2011 | Dicks et al. ................... | 381/104 |
| 2011/0201944 A1 * | 8/2011 | Higgins et al. ............... | 600/483 |
| 2012/0064497 A1 * | 3/2012 | Wu ................................ | 434/265 |

FOREIGN PATENT DOCUMENTS

| | | |
|---|---|---|
| DE | 202008016123 U1 | 2/2009 |
| WO | 2005/082454 A1 | 9/2005 |
| WO | 2006/016288 A1 | 2/2006 |

OTHER PUBLICATIONS

International Search Report and Written Opinion, Patent Cooperation Treaty, Apr. 26, 2012, 11 pages, PCT/US2011/058658, European Patent Office.

* cited by examiner

*Primary Examiner* — Kennedy Schaetzle

(74) *Attorney, Agent, or Firm* — Marger Johnson & McCollom PC

(57) ABSTRACT

Defibrillators, software and methods are provided, for issued verbal prompts to rescuers. A defibrillator may receive a muting input and, responsive thereto, cause a verbal prompt to not be issued or to be issued less loudly relative another verbal prompt.

20 Claims, 8 Drawing Sheets

METHODS

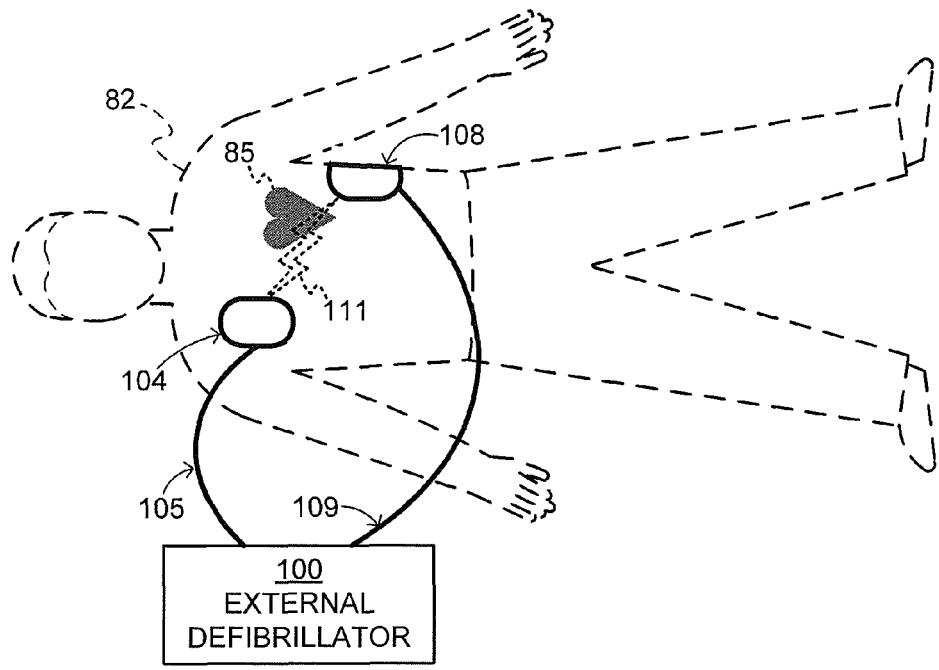
FIG. 1 *DEFIBRILLATION SCENE*
| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |
FIG. 2 *TWO MAIN TYPES OF EXTERNAL DEFIBRILLATORS*

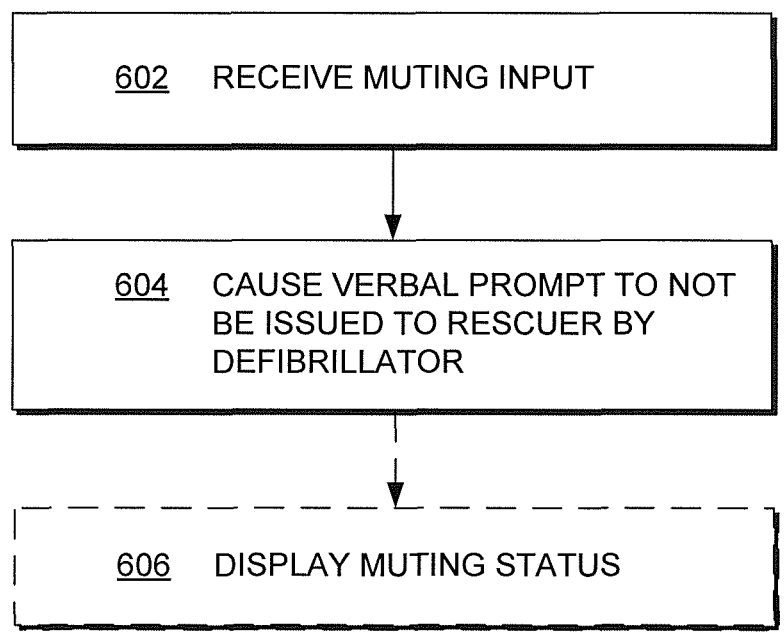
FIG. 6     *METHODS*

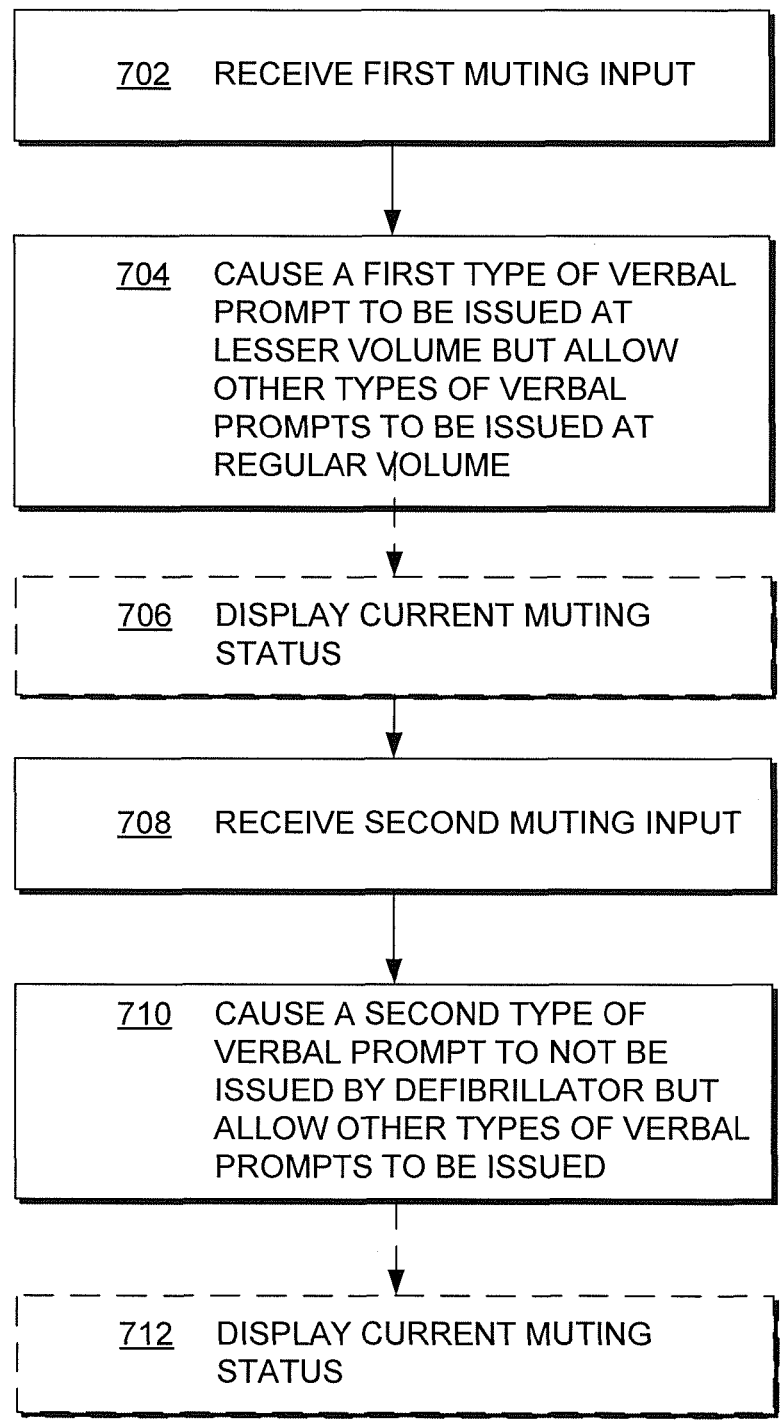
FIG. 7    METHODS

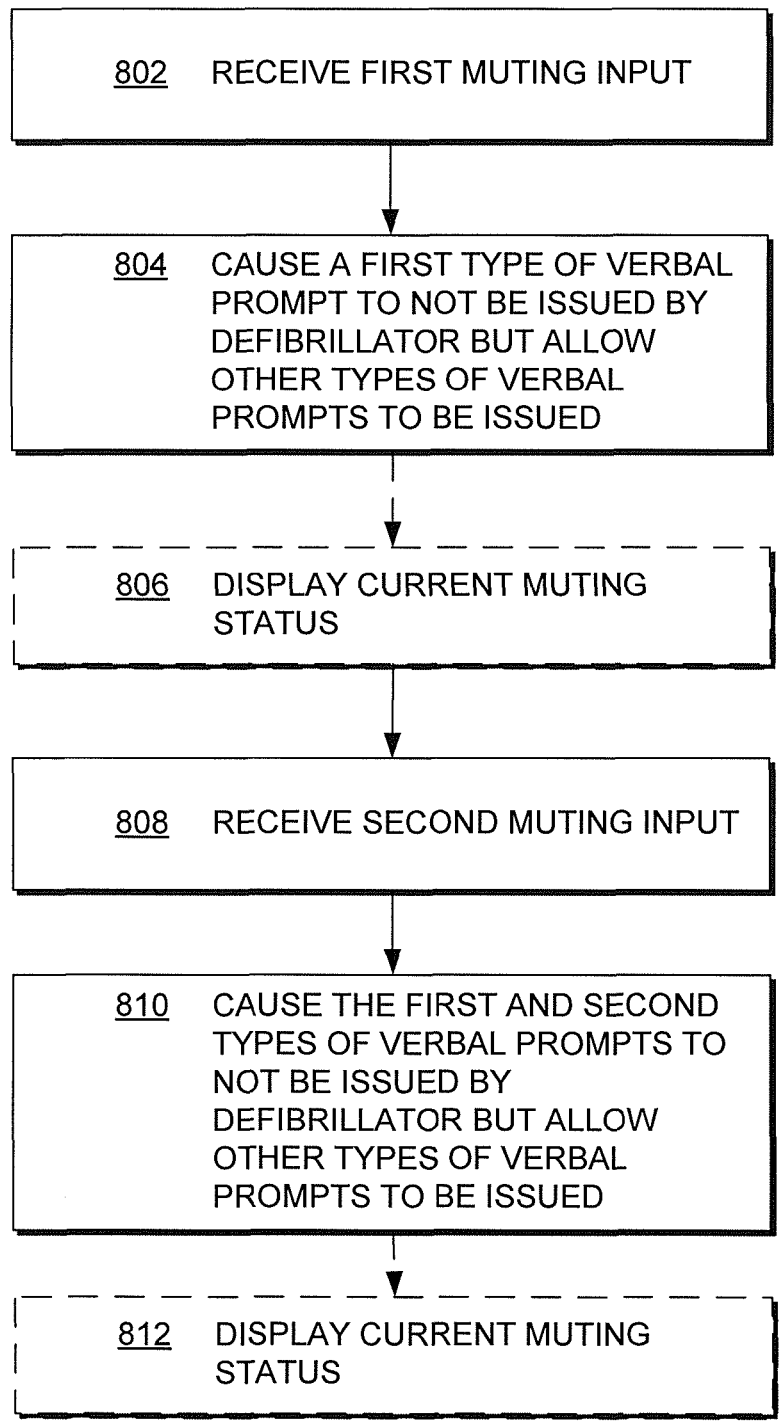
FIG. 8    METHODS

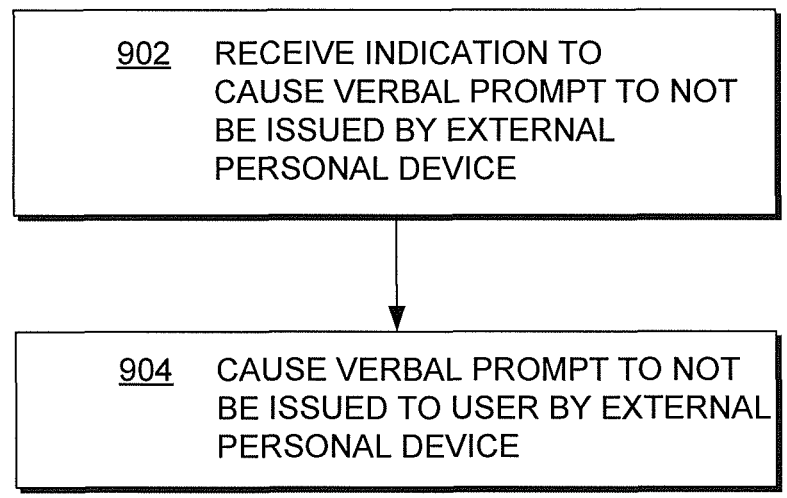
FIG. 9  *METHODS*

DEFIBRILLATOR WITH MUTABLE SOUND PROMPTS

RELATIONSHIP WITH OTHER APPLICATIONS

This patent application claims priority from U.S. Provisional Patent Application Ser. No. 61/409,053, filed on Nov. 1, 2010, the disclosure of which is hereby incorporated by reference for all purposes.

This patent application may be found to be related to U.S. patent application Ser. No. 13/016,871, titled DEFIBRILLATOR DELIVERING AUDIBLE PROMPTS TO EARPIECE, assigned to the same assignee, filed on the same day as the instant patent application.

FIELD

This invention generally relates to the field of defibrillators and resuscitation.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the right sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia, and some of it may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood. The person's condition will deteriorate rapidly and, if not reversed in time, they will die soon, e.g. within ten minutes.

Ventricular Fibrillation can often be reversed using a lifesaving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them.

During VF, the person's condition deteriorates, because the blood is not flowing to the brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved. Indeed, for patients with an extended down-time, survival rates are higher if CPR is administered prior to defibrillation.

It is desired to improve patient outcomes, by making improved decisions of when to administer therapy, such as electrical shocks, CPR, pharmaceuticals, etc. Patient outcomes are sometimes analyzed in post-event review.

BRIEF SUMMARY

The present description gives instances of medical devices, software and methods, the use of which may help overcome problems and limitations of the prior art.

In some embodiments, an external defibrillator may include a processor for causing a verbal prompt to be issued to a rescuer using the defibrillator to assist a person in connection with the defibrillator executing a protocol. The defibrillator may also include an interface for receiving a muting input. If a muting input is received, the defibrillator may cause the verbal prompt to not be issued, even though the defibrillator is executing the protocol.

In other embodiments, an external defibrillator may include a processor for causing a first type and a second type of verbal prompts to be issued to a rescuer using the defibrillator to assist the person in connection with the defibrillator executing a protocol. The defibrillator may also include an interface for receiving a muting input. If a muting input is received, the defibrillator may cause the first type of verbal prompts to be issued less loudly relative the second type even though the defibrillator is executing the protocol.

An advantage over the prior art is that one or more verbal prompts or type of verbal prompt may be muted or issued less loudly relative another verbal prompt or type of verbal prompt giving control of, for example, sounds at a rescue scene.

These and other features and advantages of this description will become more readily apparent from the following Detailed Description, which proceeds with reference to the drawings, in which:

BRIEF DESCRIPTION OF THE DRAWINGS

FIG. 1 is a diagram of a scene where an external defibrillator is used to save the life of a person according to embodiments.

FIG. 2 is a table listing two main types of the external defibrillator shown in FIG. 1, and who they might be used by.

FIG. 6 is a flowchart for illustrating a method of causing a verbal prompt to not be issued by a defibrillator according to embodiments.

FIGS. 7 and 8 are flowcharts for illustrating methods of causing one or more different types of verbal prompts to not be issued by a defibrillator according to embodiments.

FIG. 9 is a flowchart for illustrating a method of causing a verbal prompt to not be issued by an external personal device according to embodiments.

DETAILED DESCRIPTION

Figure 3:
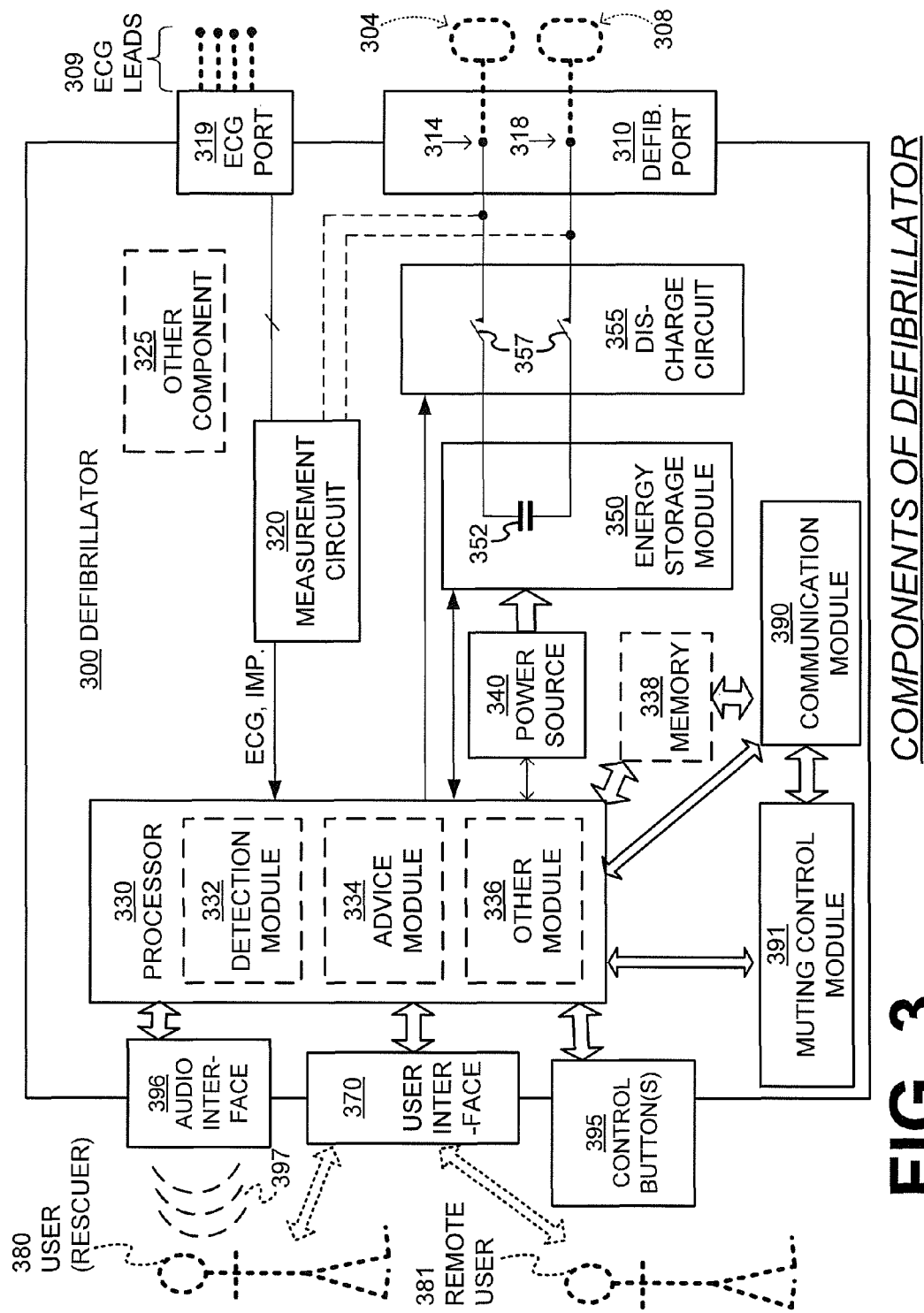
FIG. 3 is a diagram showing components of a defibrillator, such as the one shown in FIG. 1, which is made according to embodiments.

As has been mentioned, the present description is about making a decision of whether electric therapy should be administered or not. Embodiments include medical devices that can administer electrical therapy, such as defibrillators, pacers, etc. Examples are now described.

FIG. 1 is a diagram of a defibrillation scene. A person 82 is lying on their back. Person 82 could be a patient in a hospital, or someone found unconscious, and then turned to be on their back. Person 82 is experiencing a condition in their heart 85, which could be Ventricular Fibrillation (VF).

A portable external defibrillator 100 has been brought close to person 82. At least two defibrillation electrodes 104, 108 are usually provided with external defibrillator 100, and are sometimes called electrodes 104, 108. Electrodes 104, 108 are coupled with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, goes also through heart 85, in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

FIG. 2 is a table listing two main types of external defibrillators, and who they are primarily intended to be used by. A first type of defibrillator 100 is generally called a defibrillator-monitor, because it is typically formed as a unit with a patient monitor. A defibrillator-monitor is intended to be used by persons in the medical professions, such as doctors, nurses, paramedics, emergency medical technicians, etc. Such a defibrillator-monitor is intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological signals of a person in an emergency scenario. For example, these signals can include a person's full ECG (electrocardiogram) signals. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is at an Intensive Care Unit, and so on.

AEDs, however, can also be used by people who are not in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/AED training on their own initiative. This way, defibrillation can be administered soon enough after the onset of VF, to hopefully be effective in rescuing the person.

There are additional types of external defibrillators, which are not listed in FIG. 2. For example, a hybrid defibrillator can have aspects of an AED, and also of a defibrillator-monitor. A usual such aspect is additional ECG monitoring capability.

FIG. 3 is a diagram showing components of an external defibrillator 300 made according to embodiments. These components can be, for example, in external defibrillator 100 of FIG. 1.

External defibrillator 300 is intended for use by a user 380, who would be the rescuer. According to embodiments, the external defibrillator may also be used by a remote user 381 such as a physician who is currently out of town but able to communicate with the defibrillator 300 over a wired or wireless connection, for example.

Defibrillator 300 typically includes a defibrillation port 310, such as a socket. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored in defibrillator 300, as will be seen later in this document.

If defibrillator 300 is actually a defibrillator-monitor, as was described with reference to FIG. 2, then it will typically also have an ECG port 319, for plugging in ECG leads 309. ECG leads 309 can sense a full ECG signal. Moreover, a defibrillator-monitor could have additional ports (not shown), and an other component 325 for the above described additional features.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions. In addition, if other component 325 is indeed provided, it may be operated in part by processor 330, etc.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 380, etc.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, and so on.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for user 380 or remote user 381. User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

An additional feature of a defibrillator can be CPR-prompting. Prompts are issued to the user, visual or by sound, so that the user can administer CPR. Examples are taught in U.S. Pat. No. 6,334,070 and No. 6,356,785. In certain embodiments, such prompts can be issued to the user 380 as sound waves 397 emanating from an audio interface 396 such as a speaker, for example.

One or more control buttons 395 can be used to enable the user 380 to provide certain commands to the defibrillator 300 as input. Responsive to the user 380 or another user interacting with one or more of the control button(s) 395, the processor 330 can execute instructions to control the module or component to be affected based on the input. For example, the control button(s) 395 can be used to direct the processor 330 to prevent the audio interface 396 from delivering a verbal prompt or, in the alternative, deliver the verbal prompt at a reduced volume.

The defibrillator 300 can further include a muting control module 391 that can interact with the processor 330 and communication module 390. In certain embodiments, the muting control module 391 is a module in processor 330. The muting control module 391 can determine whether an audible indication such as a prompt, for example, is to not be issued to the user 380.

Figure 4:
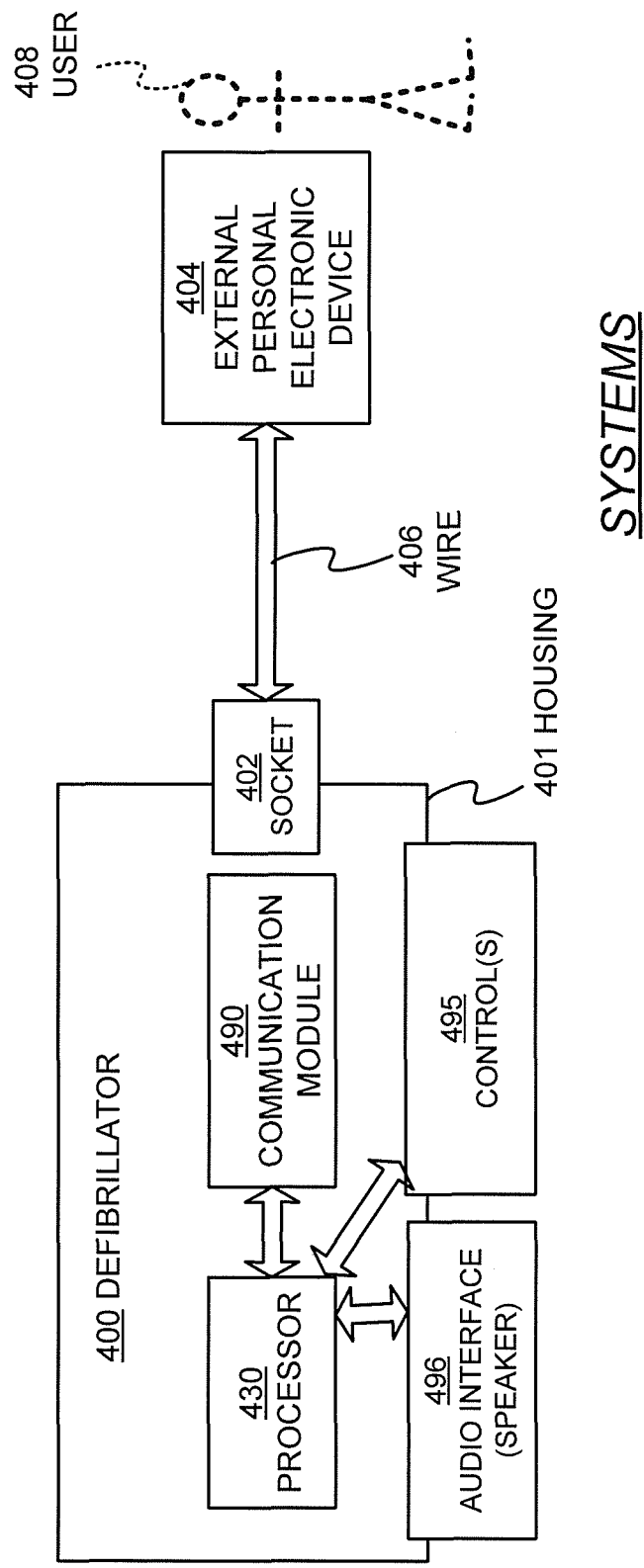
FIG. 4 is a diagram showing a defibrillator interacting with an external personal electronic device.

FIG. 4 is a diagram showing a defibrillator 400, such as the defibrillator 300 of FIG. 3, for caring for a person. Defibrillator 400 includes a housing 401 that contains an energy storage module, and also has a socket 402. An external personal electronic device 404 used by a user 408 may be connected to the defibrillator 400 by way of a wire 406 that terminates in a plug that is plugged into the socket 402. The electronic device 404 may include a personal sound device, such as an earpiece suitable to be worn by a user.

Defibrillator 400 includes a processor 430, such as the processor 330 of FIG. 3, for causing a verbal prompt to be issued to a rescuer using the defibrillator to assist the person in connection with the defibrillator executing a protocol. Defibrillator 400 may issue the verbal prompt by way of an audio interface 496, such as the audio interface 396 of FIG. 3. The audio interface 496 may include a speaker.

Defibrillator 400 may also include an interface that can be used to enable a user to provide input. The input can be instructions, to the processor 430, to a communication module 490, which may be an embodiment of the communication module 390 of FIG. 3, or both, for example. If a muting input is received, the verbal prompt that is called for by the protocol is caused to not be issued, even though the defibrillator is executing the protocol. In the example of FIG. 4, the interface includes control(s) 495. The control(s) 495 may be configured to receive a muting input, for example.

In certain embodiments, the muting input is received via the wire 406. In other embodiments, the muting input is received wirelessly from an external personal electronic device. The external personal electronic device may comprise a telephone, for example.

In certain embodiments, the processor 430 may cause two types of verbal prompts to be issued by the defibrillator 400 to a rescuer using the defibrillator 400 to assist a person in connection with the defibrillator 400 executing a protocol. In such embodiments, receiving a muting input may cause one of the two types of verbal prompts to not be issued by the defibrillator 400, but still permit the other of the two types of verbal prompts to be issued by the defibrillator 400.

Further, receiving a second muting input may cause the other of the two types verbal prompts to not be issued by the defibrillator 400. In such embodiments, the first and second muting inputs may be received sequentially. Alternatively or in addition, the first muting input may be received from one of the defibrillator 400 and the external device 404 and the second muting input may be received from the other of the defibrillator 400 and the external device 404.

In other embodiments, if the muting input is received, the first type of verbal prompt may be caused to be issued less loudly relative the second type even though the defibrillator 400 is executing the protocol.

Figure 5:
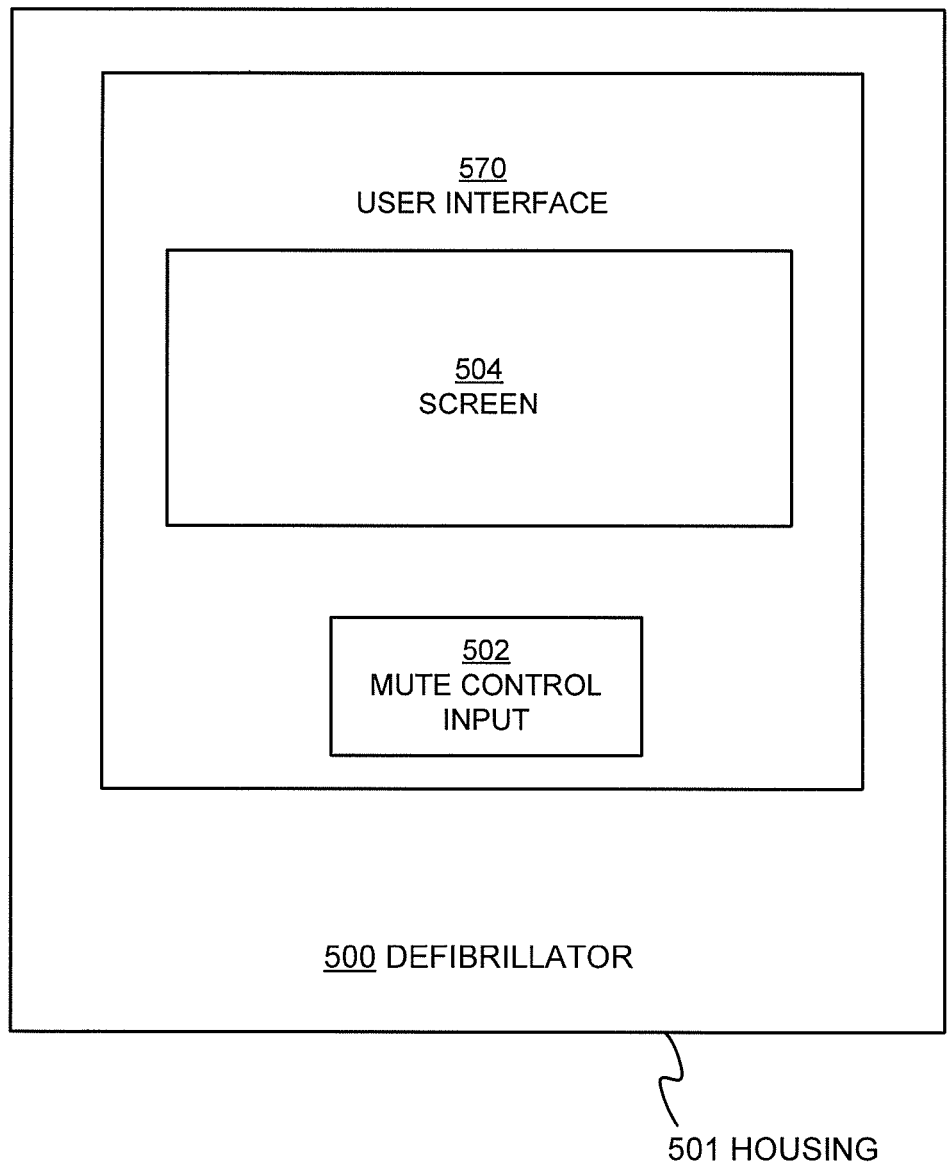
FIG. 5 is a diagram showing a defibrillator user interface that has a mute control input.

FIG. 5 is a diagram showing a defibrillator 500, such as the defibrillator 300 of FIG. 3. Defibrillator 500 has a user interface 570, such as the user interface 370, and a housing 501, such as the housing 401 of FIG. 4. The user interface 570 may include a screen 504. In such embodiments, a status of whether a muting input has been received by the defibrillator 500 may be visible on the screen 504. In addition, text and/or graphic prompts could be shown on the screen. These could be the same or abbreviated or elaborated versions of the verbal prompts. They could also be presented in different languages. They could only be shown if/when the verbal prompts are muted or reduced in volume.

In addition, the interface 570 may have a mute control input 502. The mute control input 502 may be implemented in any number of ways. For example, it may include a button, a knob, a switch, an on-screen input such as a virtual button that can be actuated by a mouse or via a touch screen, and so on.

In some embodiments, a record is being generated in connection with the defibrillator executing the protocol. The record could be generated by the on-board processor, and then exported for later use in analysis, post event review, quality control, etc. The muting input can be added to the record as an event. In some of these embodiments, a time stamp can be generated in association with receiving the muting input. In such cases, the time stamp can be added to the record as associated with the receipt of the muting input.

The functions of this description may be implemented by one or more devices that include logic circuitry. The device performs functions and/or methods as are described in this document. The logic circuitry may include a processor that may be programmable for a general purpose, or dedicated, such as microcontroller, a microprocessor, a Digital Signal Processor (DSP), etc. For example, the device may be a digital computer like device, such as a general-purpose computer selectively activated or reconfigured by a computer program stored in the computer. Alternately, the device may be implemented by an Application Specific Integrated Circuit (ASIC), etc.

Moreover, methods are described below. The methods and algorithms presented herein are not necessarily inherently associated with any particular computer or other apparatus. Rather, various general-purpose machines may be used with programs in accordance with the teachings herein, or it may prove more convenient to construct more specialized apparatus to perform the required method steps. The required structure for a variety of these machines will become apparent from this description.

In all cases there should be borne in mind the distinction between methods in this description, and the method of operating a computing machine. This description relates both to methods in general, and also to steps for operating a computer and for processing electrical or other physical signals to generate other desired physical signals.

Programs are additionally included in this description, as are methods of operation of the programs. A program is generally defined as a group of steps leading to a desired result, due to their nature and their sequence. A program is usually advantageously implemented as a program for a computing machine, such as a general-purpose computer, a special purpose computer, a microprocessor, etc.

Storage media are additionally included in this description. Such media, individually or in combination with others, have stored thereon instructions of a program made according to the invention. A storage medium according to the invention is a computer-readable medium, such as a memory, and is read by the computing machine mentioned above.

Performing the steps or instructions of a program requires physical manipulations of physical quantities. Usually, though not necessarily, these quantities may be transferred, combined, compared, and otherwise manipulated or processed according to the instructions, and they may also be stored in a computer-readable medium. These quantities include, for example electrical, magnetic, and electromagnetic signals, and also states of matter that can be queried by such signals. It is convenient at times, principally for reasons of common usage, to refer to these quantities as bits, data bits, samples, values, symbols, characters, images, terms, numbers, or the like. It should be borne in mind, however, that all of these and similar terms are associated with the appropriate physical quantities, and that these terms are merely convenient labels applied to these physical quantities, individually or in groups.

This detailed description is presented largely in terms of flowcharts, display images, algorithms, and symbolic representations of operations of data bits within at least one computer readable medium, such as a memory. Indeed, such descriptions and representations are the type of convenient labels used by those skilled in programming and/or the data processing arts to effectively convey the substance of their work to others skilled in the art. A person skilled in the art of programming may use these descriptions to readily generate specific instructions for implementing a program according to the present invention.

Often, for the sake of convenience only, it is preferred to implement and describe a program as various interconnected distinct software modules or features, individually and collectively also known as software. This is not necessary, however, and there may be cases where modules are equivalently aggregated into a single program with unclear boundaries. In any event, the software modules or features of this description may be implemented by themselves, or in combination with others. Even though it is said that the program may be stored in a computer-readable medium, it should be clear to a person skilled in the art that it need not be a single memory, or even a single machine. Various portions, modules or features of it may reside in separate memories, or even separate machines. The separate machines may be connected directly, or through a network, such as a local access network (LAN), or a global network, such as the Internet.

It will be appreciated that some of these methods may include software steps which may be performed by different modules of an overall software architecture. For example, data forwarding in a router may be performed in a data plane, which consults a local routing table. Collection of performance data may also be performed in a data plane. The performance data may be processed in a control plane, which accordingly may update the local routing table, in addition to neighboring ones. A person skilled in the art will discern which step is best performed in which plane.

An economy is achieved in the present document in that a single set of flowcharts is used to describe both programs, and also methods. So, while flowcharts are described in terms of boxes, they can mean both method and programs.

For this description, the methods may be implemented by machine operations. In other words, embodiments of programs are made such that they perform methods of the invention that are described in this document. These may be optionally performed in conjunction with one or more human operators performing some, but not all of them. As per the above, the users need not be collocated with each other, but each only with a machine that houses a portion of the program. Alternately, some of these machines may operate automatically, without users and/or independently from each other.

Methods are now described.

FIG. 6 is a flowchart for illustrating a method 600 of causing a verbal prompt to not be issued by a defibrillator according to embodiments. In an operation at 602, a muting input is received by a defibrillator. Such a muting input may be received by the defibrillator by way of a control button on the defibrillator, such as the controls 495 of FIG. 4, a user interface of the defibrillator, such as the user interface 570 of FIG. 5, or an electronic device, such as the external personal electronic device 404 of FIG. 4.

In an operation at 604, the defibrillator causes a verbal prompt to not be issued to a rescuer by the defibrillator. In certain embodiments, the defibrillator may cause only a single verbal prompt to not be issued to the rescuer and then resume issuing verbal prompts to the rescuer. In other embodiments, the defibrillator may cause all verbal prompts to not be issued to the rescuer until another action occurs, such as the defibrillator receiving another muting input, for example. The verbal prompt that is not issued is ordinarily called for to be issued by the resuscitation protocol that the defibrillator is executing. But operation 604 overrides the protocol that way.

In an operation at 606, the defibrillator may optionally display a muting status indicating whether the defibrillator is currently causing one or more verbal prompts to not be issued to the rescuer. For example, a user interface of the defibrillator, such as the user interface 570 of FIG. 5, may provide a visual indication that a muting input has been received and that one or more verbal prompts are not being issued to the rescuer even though the defibrillator is executing a protocol. In certain embodiments, the indication may include an icon or a message displayed on the user interface, and so on, as also per the above.

Alternatively or in addition thereto, a light or other indicator on or in the housing of the defibrillator may activate to indicated that a muting input has been received and that one or more prompts are not being issued to the rescuer even though the defibrillator is executing a protocol.

FIG. 7 is a flowchart for illustrating a first method 700 of causing one or more different types of verbal prompts to not be issued by a defibrillator according to embodiments. In an operation at 702, a first muting input is received by a defibrillator. The first muting input may correspond to a first type of verbal prompt.

In an operation at 704, the defibrillator causes a first type of verbal prompt to be issued to a rescuer by the defibrillator at a lesser volume but allows other types of verbal prompts to be issued to the rescuer by the defibrillator at a regular volume. The volume can be lesser but still audible; or lesser enough to be practically inaudible, or entirely muted.

In an operation at 706, the defibrillator optionally displays a current muting status by way of a user interface or other indicator situated on or in the housing of the defibrillator, for example. The muting status may indicate that the defibrillator is currently issuing a certain type of verbal prompt at a reduced volume.

In an operation at 708, a second muting input is received by the defibrillator. The second muting input may correspond to a second type of verbal prompt.

In an operation at 710, the defibrillator causes a second type of verbal prompt to not be issued to the rescuer by the defibrillator but allows other types of verbal prompts to be issued to the rescuer by the defibrillator at a regular volume.

In an operation at 712, the defibrillator optionally displays a current muting status. This can be implemented in any number of ways, for example by way of the user interface or other indicator situated on or in the housing of the defibrillator, and so on, and as also per the above. For example, the muting status may provide the rescuer or other user with an indication that the defibrillator is currently causing a certain type of verbal prompt to not be issued but issuing other types of verbal prompts.

FIG. 8 is a flowchart for illustrating a second method 800 of causing one or more different types of verbal prompts to not be issued by a defibrillator according to embodiments. In an operation at 802, a first muting input is received by a defibrillator. The first muting input may correspond to a first type of verbal prompt.

In an operation at 804, the defibrillator causes a first type of verbal prompt to not be issued to a rescuer by the defibrillator but allows other types of verbal prompts to be issued to the rescuer by the defibrillator.

In an operation at 806, the defibrillator optionally displays a current muting status by way of a user interface or other indicator situated on or in the housing of the defibrillator, for example. The muting status may indicate that the defibrillator is currently causing a certain type of verbal prompt to not be issued to the rescuer, and so on, and as also per the above.

In an operation at 808, a second muting input is received by the defibrillator. The second muting input may correspond to a second type of verbal prompt.

In an operation at 810, the defibrillator causes both the first type of verbal prompt and a second type of verbal prompt to not be issued to the rescuer by the defibrillator but allows other types of verbal prompts to be issued to the rescuer by the defibrillator.

In an operation at 812, the defibrillator optionally displays a current muting status by way of the user interface or other indicator situated on or in the housing of the defibrillator. For example, the muting status may provide the rescuer or other user with an indication that the defibrillator is currently causing two types of verbal prompt to not be issued but issuing other types of verbal prompts.

FIG. 9 is a flowchart for illustrating a method 900 of causing a verbal prompt to not be issued by an external personal device according to embodiments. In an operation at 902, a defibrillator, such as the defibrillator 400 of FIG. 4, receives an indication to cause a verbal prompt to not be issued by an external device, such as the external personal electronic device 404 of FIG. 4.

In an operation at 904, the defibrillator causes the verbal prompt to not be issued by the external device. In situations where there are multiple types of verbal prompt, a first type of verbal prompt may be caused to be muted entirely. In certain embodiments, the defibrillator may cause only a single verbal prompt or type of verbal prompt to not be issued by the external device and then allow the external device to resume issuing verbal prompts. In other embodiments, the defibrillator may cause all verbal prompts to not be issued by the external device until another action occurs, such as the defibrillator receiving an other indication, for example.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems.

The following claims define certain combinations and sub-combinations of elements, features, steps, and/or functions, which are regarded as novel and non-obvious. Additional claims for other combinations and sub-combinations may be presented in this or a related document.

What is claimed is:

1. An external defibrillator comprising:
an energy storage module configured to store an electrical charge;
a defibrillation port configured to guide via electrodes stored electrical charge to a person;
a processor configured to cause a verbal prompt to be issued to a rescuer using the defibrillator in connection with the defibrillator executing a protocol; and
an interface configured to receive a muting input, in which
if a first muting input is received via the interface, the verbal prompt is caused to not be issued even though the defibrillator is executing the protocol, in which
the processor can cause at least two types of verbal prompts to be issued, in which
receiving the first muting input causes one of the two types of verbal prompts to not be issued but still permits the other of the two types of verbal prompts to be issued, and in which
receiving a second muting input causes the other of the two types verbal prompts to not be issued.

2. The external defibrillator of claim 1, in which
the first and second muting inputs are received sequentially.

3. The external defibrillator of claim 1, in which
the first muting input is received from one of the defibrillator and an external device, and
the second muting input is received from the other of the defibrillator and the external device.

4. An external defibrillator comprising:
an energy storage module configured to store an electrical charge;
a defibrillation port configured to guide via electrodes stored electrical charge to a person;
a processor configured to cause a verbal prompt to be issued to a rescuer using the defibrillator in connection with the defibrillator executing a protocol;
an interface configured to receive a muting input by which a user selectively controls issuance of the verbal prompt,
in which, if the muting input is received, the verbal prompt is caused to not be issued even though the defibrillator is executing the protocol,
further in which the muting input is received via a wire;
a housing that contains the energy storage module; and
a socket in the housing,
in which the wire terminates in a plug that is plugged in the socket.

5. An external defibrillator comprising:
an energy storage module configured to store an electrical charge;
a defibrillation port configured to guide via electrodes stored electrical charge to a person;
a processor configured to cause a verbal prompt to be issued to a rescuer using the defibrillator in connection with the defibrillator executing a protocol; and
an interface configured to receive a muting input by which a user selectively controls issuance of the verbal prompt,
in which, if the muting input is received, the verbal prompt is caused to not be issued even though the defibrillator is executing the protocol
further in which the muting input is received via a wire, in which
the wire is coupled to an external device.

6. An external defibrillator comprising:
an energy storage module configured to store an electrical charge;

a defibrillation port configured to guide via electrodes stored electrical charge to a person;

a processor configured to cause a first type and a second type of verbal prompts to be issued to a rescuer using the defibrillator in connection with the defibrillator executing a protocol; and an interface configured to receive a muting input, in which, if the muting input is received, the first type of verbal prompts is caused to be issued less loudly relative the second type even though the defibrillator is executing the protocol.

7. The external defibrillator of claim 6, in which the first type of verbal prompts is caused to be muted entirely.

8. The external defibrillator of claim 6, in which the interface includes a screen, and a status of whether the muting input has been received is visible on the screen.

9. The external defibrillator of claim 6, in which the interface includes one or more of a button, a knob, a switch, or an on-screen input.

10. The external defibrillator of claim 6, in which the muting input is received wirelessly from an external personal electronic device.

11. The external defibrillator of claim 10, in which the external personal electronic device comprises a telephone.

12. The external defibrillator of claim 6, in which receiving the muting input causes one of the first and second types of verbal prompts to not be issued, but still permits the other of the first and second types of verbal prompts to be issued.

13. The external defibrillator of claim 6, in which the interface is configured to receive the muting input via a wire.

14. The external defibrillator of claim 13, further comprising:

a housing that contains the energy storage module;
a socket in the housing, and
in which the wire terminates in a plug that is plugged in the socket.

15. The external defibrillator of claim 13, in which the wire is coupled to an external device.

16. The external defibrillator of claim 6, in which the processor is configured to generate a record in connection with the defibrillator executing the protocol, and the processor is further configured to add the muting input to the record.

17. The external defibrillator of claim 16, in which the processor is configured to generate a time stamp in association with receiving the muting input, and the processor is further configured to add the time stamp to the record as associated with the receipt of the muting input.

18. An external defibrillator comprising:

an energy storage module configured to store an electrical charge;

a defibrillation port configured to guide via electrodes stored electrical charge to a person;

a processor configured to cause a first type and a second type of verbal prompts to be issued to a rescuer using the defibrillator in connection with the defibrillator executing a protocol; and an interface configured to receive a muting input, in which
even though the defibrillator is executing the protocol, receiving a first muting input causes one of the first and second types of verbal prompts to not be issued but still permits the other of the first and second types of verbal prompts to be issued, and in which receiving a second muting input causes the other of the first and second types verbal prompts to not be issued.

19. The external defibrillator of claim 18, in which the first and second muting inputs are received sequentially.

20. The external defibrillator of claim 18, in which the first muting input is received from one of the defibrillator and an external device, and the second muting input is received from the other of the defibrillator and the external device.

* * * * *